United States Patent
Han et al.

(10) Patent No.: US 7,973,285 B2
(45) Date of Patent: Jul. 5, 2011

(54) APPARATUS FOR DETECTING THE LEAKAGE OF HEAVY WATER IN NUCLEAR REACTOR SYSTEM AND DETECTION METHOD USING THE SAME

(75) Inventors: Jae Min Han, Daejeon (KR); Do Young Jeong, Daejeon (KR); Kwang Hoon Ko, Daejeon (KR); Taek Soo Kim, Daejeon (KR)

(73) Assignees: Korea Atomic Energy Research Institute, Daejeon (KR); Korea Hydro & Nuclear Power Co., Ltd., Seoul (KR)

( * ) Notice: Subject to any disclaimer, the term of this patent is extended or adjusted under 35 U.S.C. 154(b) by 0 days.

(21) Appl. No.: 12/616,364

(22) Filed: Nov. 11, 2009

(65) Prior Publication Data
US 2010/0118294 A1    May 13, 2010

(30) Foreign Application Priority Data
Nov. 13, 2008  (KR) .................. 10-2008-0112620

(51) Int. Cl.
*G01J 5/02*          (2006.01)
(52) U.S. Cl. .................................................. 250/339.1
(58) Field of Classification Search ............ 250/339.01–339.15, 338.1–338.4, 340, 341.1–341.8
See application file for complete search history.

(56) References Cited

U.S. PATENT DOCUMENTS

| | | | |
|---|---|---|---|
| 3,925,666 A | | 12/1975 | Allan et al. |
| 5,047,639 A | * | 9/1991 | Wong .......................... 250/341.1 |
| 5,341,214 A | * | 8/1994 | Wong .............................. 356/437 |
| 5,408,883 A | * | 4/1995 | Clark et al. ...................... 73/601 |
| 2002/0126269 A1 | * | 9/2002 | Sato ................................. 355/77 |

FOREIGN PATENT DOCUMENTS

| | | | |
|---|---|---|---|
| DE | 2356597 A | * | 5/1974 |
| JP | 56016834 A | | 2/1981 |
| JP | 7063876 A | | 3/1995 |

(Continued)

OTHER PUBLICATIONS

Tam et al., "Optical absorption of light and heavy water by laser optoacoustic spectroscopy," 1979, Applied Optics, Vo. 18, No. 19, pp. 3348-3358.*

(Continued)

*Primary Examiner* — David P Porta
*Assistant Examiner* — Kiho Kim
(74) *Attorney, Agent, or Firm* — The Webb Law Firm

(57) ABSTRACT

An apparatus and a method for detecting a leakage of heavy water in a nuclear reactor system includes: a diode laser that injects a generated laser beam to a test sample placed in a light absorption cell; a vacuum pump adjusts a degree of vacuum in the light absorption cell; a test sample introduction unit gathers an air test sample from a location with a high possibility of a leakage of heavy water or a light water test sample from a secondary side of a steam generator and transfers the sample to the light absorption cell; an optical detector detects the laser beam which has passed through the light absorption cell; and a microprocessor controls the operation of the diode laser, the vacuum pump, the test sample introduction unit, and the optical detector, receives a detect signal from the optical detector, and analyzes an absorption spectrum signal.

17 Claims, 3 Drawing Sheets

FOREIGN PATENT DOCUMENTS

| JP | 9043090 A | 2/1997 |
| KR | 1020080038908 A | 5/2008 |

OTHER PUBLICATIONS

Cline et al., "The secondary response distortion in transient absorption spectroscopy," 2002, Review of Scientific Instruments, vol. 73, No. 11, pp. 3908-3915.*

Choi, Seung Yeol et al., "Feasibility of Fourier Transform (FT) Infrared spectroscopy for monitoring heavy water concentration in pressurized heavy water reactor", Vibrational Spectroscopy, 2003, pp. 251-256, vol. 31, Elsevier Science B.V.

Kalyanasundaram, P. et al., "Acoustic Emission Technique for Leak Detection in an End Shield of a Pressurised Heavy Water Reactor", Int. J. Pres. Ves. & Piping, 1989, pp. 65-74, vol. 36, Elsevier Science Publishers Ltd., England.

* cited by examiner

APPARATUS FOR DETECTING THE LEAKAGE OF HEAVY WATER IN NUCLEAR REACTOR SYSTEM AND DETECTION METHOD USING THE SAME

CROSS-REFERENCE TO RELATED APPLICATIONS

This application claims the priority of Korean Patent Application No. 2008-0112620 filed on Nov. 13, 2008, in the Korean Intellectual Property Office, the disclosure of which is incorporated herein by reference.

BACKGROUND OF THE INVENTION

1. Field of the Invention

The present invention relates to an apparatus for detecting a leakage of heavy water in a nuclear reactor system and a method for detecting a leakage of heavy water using the same, and more particularly, to an apparatus for detecting a leakage of heavy water in a nuclear reactor system capable of sensitively monitoring a leakage of heavy water within a nuclear reactor system by sampling the air or by sampling a secondary side of a steam generator in real time by taking an air test sample around a pressure tube or a delayed neutron tube of the nuclear reactor system or a test sample from the secondary side of the steam generator, and detecting and measuring the concentration of mixed heavy water molecules by using the laser absorption spectroscopy, and a method for detecting a leakage of heavy water using the same.

2. Description of the Related Art

A leakage of heavy water in nuclear energy (or atomic power) facilities has a direct connection with a leakage of radioactivity, critically affecting the stability of a nuclear energy production facility. In particular, because a heavy water nuclear reactor system is made up of 380 or more pressure tubes, and numerous pipes are installed in a complicated manner, the detection and monitoring of a heavy water leakage is crucial.

The related art method for detecting a leakage of heavy water in a nuclear reactor system includes an infrared spectrometry method, a radiation monitoring method, a mass spectroscopy method, and the like.

The infrared spectrometry method is a heavy water leakage detection method using the qualities of components of a material that vibrate while absorbing a particular wavelength when irradiated by an infrared ray.

Namely, when an infrared ray irradiates the material, its components vibrate while absorbing a particular wavelength of the infrared ray, and as a result, as an infrared spectrum measured after the irradiation has a pattern in which absorption has occurred in a particular wavelength region causing such molecular vibration, qualitative analysis and quantitative analysis of the material can be possibly performed based on such spectrum analysis.

Heavy water, ($D_2O$), within the nuclear reactor system, refers to a combination of two heavy hydrogen atoms ($^2H$ or D) having a mass number of 2 with oxygen (O), and light water, ($H_2O$) refers to a combination of two hydrogen atoms ($^1H$) having a mass number of 1 with oxygen (O).

When heavy water within the nuclear reactor system leaks and meets light water, the heavy water is mostly changed from $D_2O$ to mixed heavy water (HDO) due to collision reaction between heavy water and light water. The infrared spectrometry determines whether or not heavy water has leaked by measuring the density of heavy water in light water by using the difference between the infrared absorption characteristics of the heavy water and that of the light water (Seung Yeol Cho, et al. Vibrational Spectroscopy 31, 251 (2003)). The infrared spectrometry method can employ FT-IR (Fourier Transform Infrared) equipment commercially on sale, does not require to pre-process a test sample, and its operation is easy. However, this method is disadvantageous in that measurement sensitivity is low, analysis of an air test sample is not possible, and it is not possible to measure heavy water leaked into the air.

The radiation monitoring method is mainly concerned with measuring beta radiation radioactivity having weak energy. In this method, radioactivity caused by tritium ($^3H$ or T) leaked to a secondary side with heavy water is measured within light water to monitor whether or not the heavy water has leaked.

Tritium used for a heavy water leakage detection method using a liquid scintillation counting method, which is a radio-isotope of hydrogen having a mass number of 3, is a pure beta-emitting radionuclide having a half-life of 12.35 years and emitting beta rays with energy of an average 5.7 KeV.

The tritium is generated as the heavy hydrogen present in a great quantity of heavy water present in a primary side is reacted with a neutron, and the density of the tritium generated thusly in the primary side increases as an operational time of nuclear power plants increases. Thus, it may be determined whether or not the heavy water within the primary side has leaked to the secondary side by monitoring whether or not the density of the tritium within the secondary side increases.

However, although the liquid scintillation counting method has a high sensitivity in the heavy water leakage measurement, it disadvantageously incurs a great deal of maintenance and repair cost, generates a harmful waste scintillation liquid, and is extremely difficult to utilize as a real time monitoring apparatus.

The mass spectroscopy method, which determines whether or not heavy water has leaked by deoxidizing water molecules to generate hydrogen molecules and measuring an isotope ratio of H and D of hydrogen molecules, is advantageous in that it has a high level of measurement sensitivity, but it requires a high-priced, high resolving power mass analyzer of a double focusing magnetic sector type having a mass resolving power of 2000 or higher, requires a complicated test sample preprocessing procedure for deoxidizing HDO molecules into HD molecules, and is not suitable for a real time monitoring apparatus.

Besides the above-mentioned methods, whether or not heavy water has leaked may also be determined by measuring an acoustic wave generated when heavy water has leaked in the air (P. Kalyanasundaram, et al. International Journal of Pressure Vessels and Piping 36, 65 (1989)). However, this indirect acoustic wave measurement method has difficulty in discriminating between acoustic wave caused by a leakage of heavy water and ambient noise, and has a low level of sensitivity. In addition, because this method is a contact type method, there is a limitation in its employment, and further, it cannot detect a leakage of heavy water from a steam generator.

SUMMARY OF THE INVENTION

An aspect of the present invention provides an apparatus for detecting a leakage of heavy water in a nuclear reactor system capable of detecting in real time a leakage of heavy water such as a leakage of heavy water from a pressure tube or a delayed neutron tube of a nuclear reactor system as well as a leakage of heavy water from a steam generator by sampling the air and using a highly sensitive process of laser absorption spectroscopy (LAS).

Another aspect of the present invention provides an apparatus for detecting a leakage of heavy water in a nuclear reactor system, which can be manufactured at a low cost by employing a low-priced small diode laser and which is readily portable due to its small size.

According to an aspect of the present invention, there is provided an apparatus for detecting a leakage of heavy water in a nuclear reactor system, including: a diode laser generating a laser beam and injecting the generated laser beam into a test sample placed in a light absorption cell; the light absorption cell accommodating a gathered test sample therein; a vacuum pump adjusting a degree of vacuum of the light absorption cell; a test sample introduction unit gathering an air test sample from a location with a high possibility of a leakage of heavy water, or a light water test sample from a secondary side and transferring it to the light absorption cell; an optical detector detecting a laser beam which has passed through the light absorption cell; and a microprocessor controlling the operation of the diode laser, the light absorption cell, the vacuum pump, the test sample introduction unit, and the optical detector, receiving a detection signal from the optical detector, and analyzing an absorption spectrum signal.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
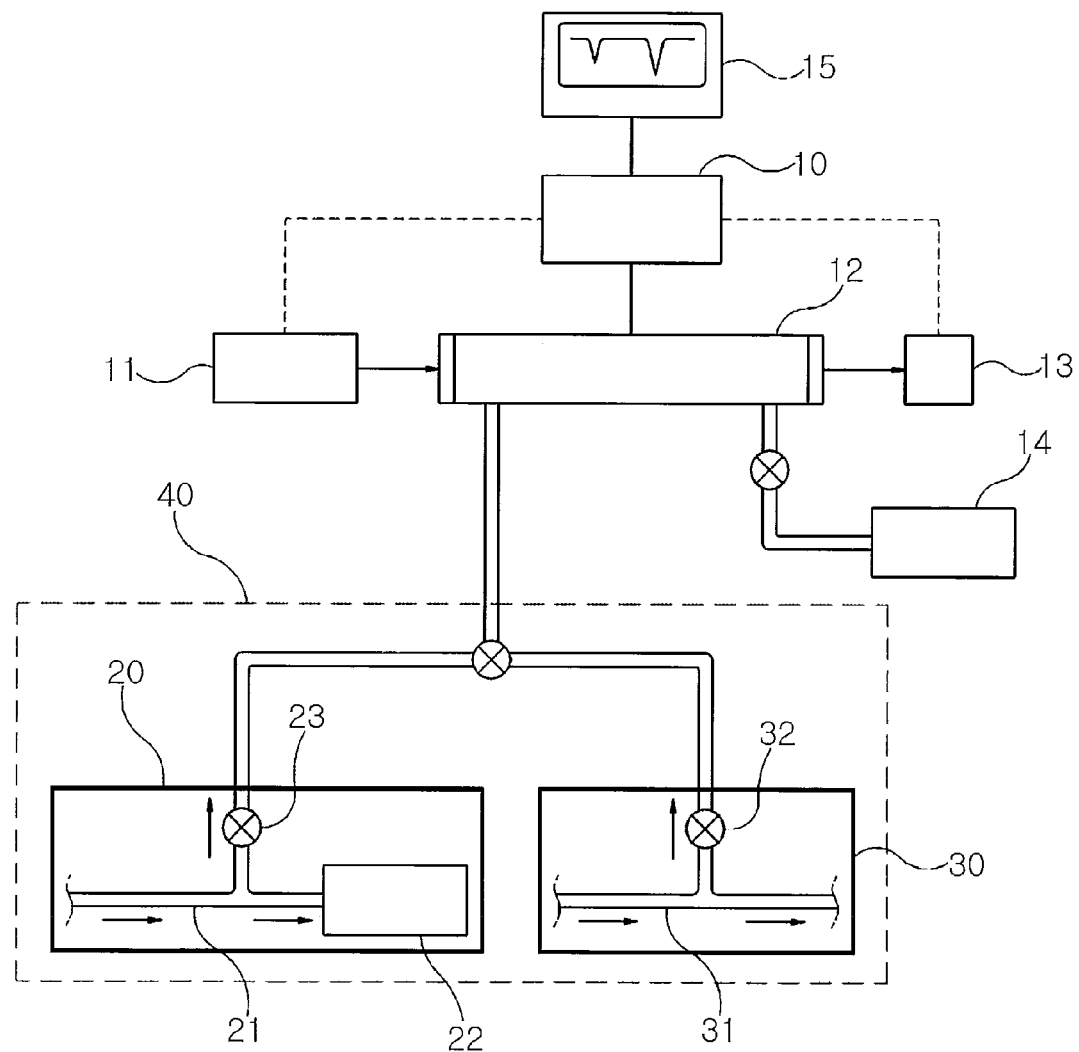
FIG. 1 is a schematic block diagram of an apparatus for detecting a leakage of heavy water in a nuclear reactor system according to an exemplary embodiment of the present invention.

Exemplary embodiments of the present invention will now be described in detail with reference to the accompanying drawings. The invention may, however, be embodied in many different forms and should not be construed as being limited to the embodiments set forth herein. Rather, these embodiments are provided so that this disclosure will be thorough and complete, and will fully convey the scope of the invention to those skilled in the art. In the drawings, the shapes and dimensions may be exaggerated for clarity, and the same reference numerals will be used throughout to designate the same or like components.

FIG. 1 is a schematic block diagram of an apparatus for detecting a leakage of heavy water in a nuclear reactor system according to an exemplary embodiment of the present invention.

With reference to FIG. 1, the apparatus for detecting a leakage of heavy water in a nuclear reactor system according to an exemplary embodiment of the present invention includes a diode laser 11 that generates a laser beam and injects the generated laser beam to a test sample placed in a light absorption cell 12; the light absorption cell 12 that accommodates a gathered test sample therein; a vacuum pump 14 that adjusts a degree of vacuum of the light absorption cell 12; a test sample introduction unit 40 that gathers an air test sample from a location with a high possibility of a leakage of heavy water or a light water test sample from a secondary side and transfers it to the light absorption cell 12; an optical detector 13 that detects a laser beam which has passed through the light absorption cell 12; a microprocessor 10 that controls the operation of the diode laser 11, the light absorption cell 12, the vacuum pump 14, the test sample introduction unit 40, and the optical detector 13, receives a detection signal from the optical detector 13, and analyzes an absorption spectrum signal; and an output unit 15 that outputs the results obtained by analyzing the absorption spectrum signal.

The diode laser 11 generates a laser beam used for analyzing a laser absorption spectrum. The diode laser 11 generates a laser beam of a near infrared ray region having a frequency range from 5,000 $cm^{-1}$ to 10,000 $cm^{-1}$, and projects the laser beam to the light absorption cell 12 having the test sample accommodated therein.

The light absorption cell 12, accommodating the gathered test sample for a laser absorption spectrum analysis, may be configured as a multi-pass cell including two or more optical mirrors, or as an optical cavity.

The vacuum pump 14 is connected with the light absorption cell 12 to maintain the degree of vacuum in the interior of the light absorption cell 12 at the level of a few Torr.

The test sample introduction unit 40 for receiving the gathered test sample is connected with the light absorption cell 12. The test sample introduction unit 40 includes a first test sample introduction part 20 for introducing an air test sample and a second test sample introduction part 30 for gathering a test sample of a secondary side of the nuclear reactor system such as a steam generator or a heat exchanger and introducing it.

The first test sample introduction part 20, which serves to detect whether or not heavy water has leaked into the air, includes an intake tube 21 for gathering and introducing a test sample, and an intake pump 22 for gathering a remote air test sample and injecting it into the light absorption cell 12.

Several intake tubes of the first test sample introduction part 20 may be installed at several locations of the nuclear reactor system to alternately inject an air test sample taken in from each location into the light absorption cell 12 to allow for analysis of the test sample, thus obtaining information regarding a leakage location of heavy water. To this end, each intake tube 21 includes a switching valve 23 for sequentially regulating test sampling gathering and a valve control unit (not shown).

The second test sample introduction part 30 serves to detect whether or not heavy water has leaked to the secondary side of the nuclear reactor system such as the steam generator or the heat exchanger. The second test sample introduction part 30 is directly connected with a light water pipe 31 of the heat exchanger of the steam generator of the nuclear reactor system and includes a switching valve 32 for controlling the introduction of a test sample and a valve control unit (not shown).

The first test sample introduction part 20 and the second test sample introduction part 30 may be separately provided in each of apparatuses for detecting a leakage of heavy water in a nuclear reactor system in order to detect whether or not heavy water has leaked. Alternately, both the first test sample introduction part 20 and the second test sample introduction part 30 may be provided in a single apparatus for detecting a leakage of heavy water in order to sequentially detect whether or not heavy water has leaked in nuclear power plant facilities through valve controlling.

The optical detector 13 measures a laser signal which has passed through the light absorption cell 12. When the air test sample introduced through the test sample introduction unit 40 is accommodated in the light absorption cell 12, a laser beam generated from the diode laser 11 is projected into the light absorption cell 12 with the test sample accommodated therein, and a signal of the laser beam which has passed through the light absorption cell 12 is measured by the optical detector 13. The signal measured by the optical detector 13 is transferred to and processed in the microprocessor 10 connected with the optical detector 13.

The microprocessor 10 controls the operation of the diode laser 11, the light absorption cell 12, the vacuum pump 14, the test sample introduction unit 40, and the optical detector 13, receives the signal which has been detected by the optical detector 13 to analyze an absorption spectrum signal, and transmits the analyzed measurement results to the output unit 15. Also, if a plurality of test sample introduction units or a plurality of intake tubes 21 are provided, the microprocessor 10 regulates the order of gathering test samples by controlling the switching valves 23 and 32 provided at each of the test sample introduction units 40 or each of the intake tubes 21.

The measurement results obtained through analysis by the microprocessor 10 are output in the form of quantified numerical values, a graph, or the like, through the output unit 15. The output unit 15 may be configured as a monitor, a printing unit, or the like.

Figure 2:
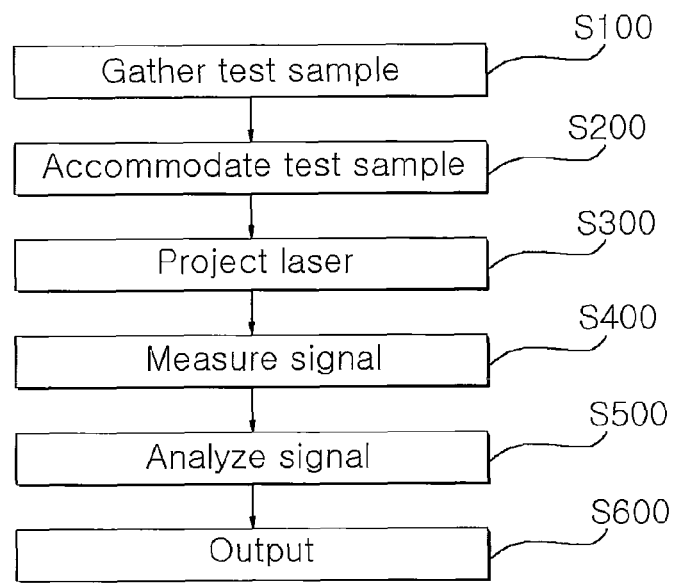
FIG. 2 is a flow chart illustrating the process of a method for detecting whether or not heavy water has leaked by using the apparatus for detecting a leakage of heavy water in a nuclear reactor system according to an exemplary embodiment of the present invention.
Figure 3:
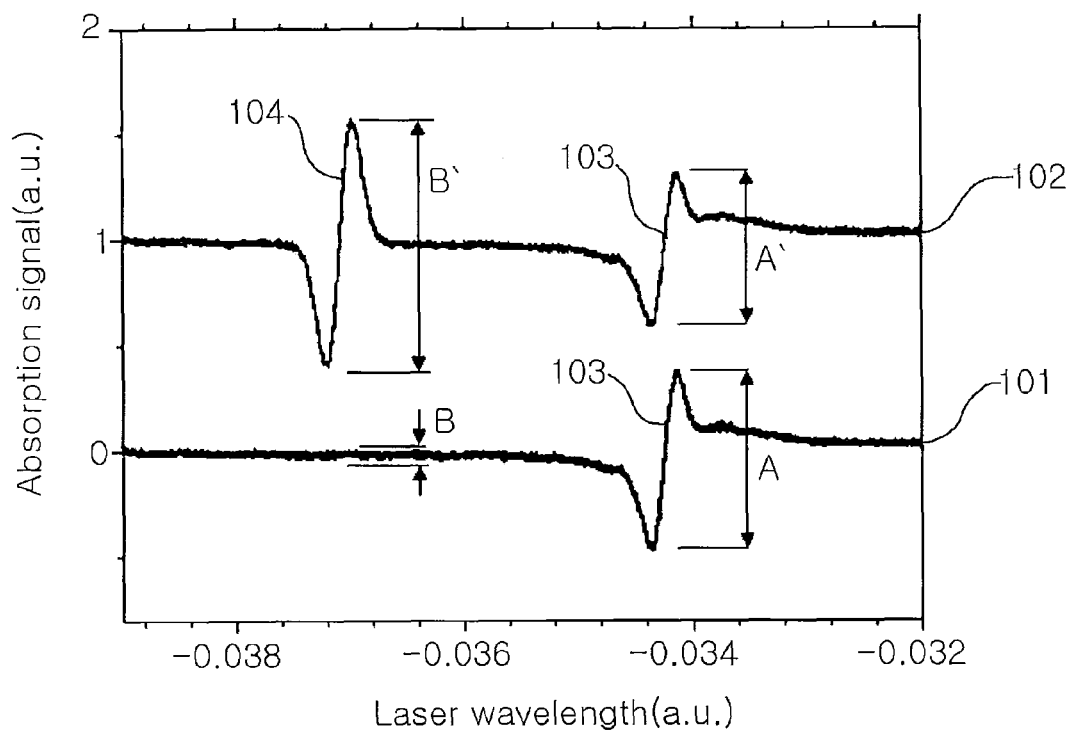
FIG. 3 illustrates a diode laser absorption spectrum measured by injecting an air test sample into a light absorption cell.
Figure 4:
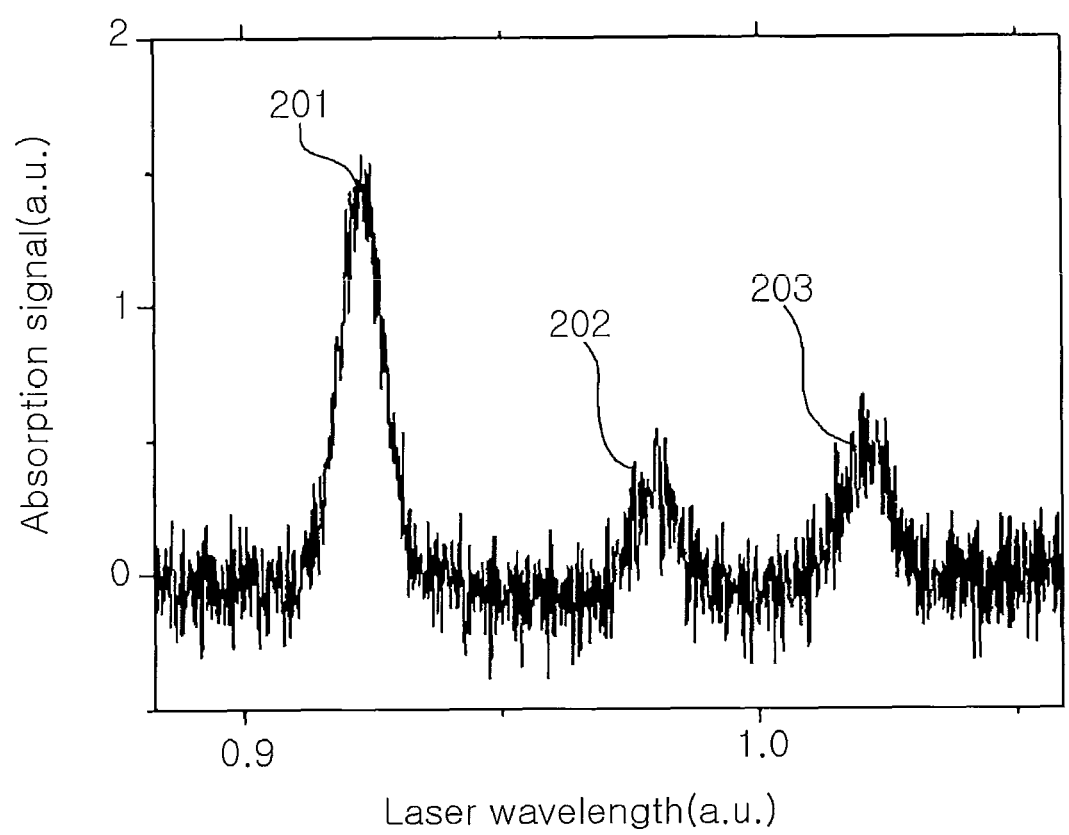
FIG. 4 illustrates a diode laser absorption spectrum obtained by measuring HDO contained in natural light water.

FIG. 2 is a flow chart illustrating the process of a method for detecting whether or not heavy water has leaked by using the apparatus for detecting a leakage of heavy water in a nuclear reactor system according to an exemplary embodiment of the present invention, FIG. 3 illustrates a diode laser absorption spectrum measured by injecting an air test sample into a light absorption cell, and FIG. 4 illustrates a diode laser absorption spectrum obtained by measuring HDO contained in natural light water.

With reference to FIG. 2, in order to detect whether or not heavy water has leaked by using the heavy water leakage detection apparatus according to the exemplary embodiment of the present invention, first, an air test sample from a location with a high possibility of a leakage of heavy water or a light water test sample of the secondary side is gathered through the test sample introduction unit 40 (S100).

As for the air test sample, a plurality of intake tubes 21 may be installed at locations with a high possibility of a leakage of heavy water or at locations suspected of having the possibility of heavy water leakage, and air test samples taken in from each location may be alternately injected into the light absorption cell 12 so as to be analyzed, thereby recognizing whether or not heavy water has leaked or an accurate leakage location. The light water test sample may be gathered by directly connecting to a tube along which light water flows within the steam generator or the heat exchanger.

In the case where test samples are gathered from several locations, test sample gathering is sequentially regulated. Namely, an analysis-completed test sample from a previous stage is removed before a new test sample is introduced, to thereby prevent the test samples from being mixed.

Next, in order to analyze the gathered test sample by using the laser absorption spectroscopy (LAS) process, the gathered test sample is introduced into the light absorption cell 12 (S200).

When the introduction of the test sample is completed, a laser beam is projected into the test sample-accommodating light absorption cell 12 through the diode laser 11 (S300). In this case, the utilized laser beam is in a near infrared ray region having a frequency ranging from 5,000 $cm^{-1}$ to 10,000 $cm^{-1}$.

The signal of the laser beam which has passed through the light absorption cell 12 is measured by the optical detector 13 (S400), and the measured signal is transmitted to the microprocessor 10 so as to be analyzed (S500).

If heavy water ($D_2O$) from the nuclear reactor system has leaked in the air, a hydrogen isotope exchange reaction is created with light water ($H_2O$) vapor in the air. If heavy water has leaked from the steam generator or from the heat exchanger and flows to light water of the secondary side, a hydrogen isotope exchange reaction is created with light water so as to be changed into 2HDO. In this case, a chemical change formula is $D_2O+H_2O \leftarrow k_1 \rightarrow 2HDO$.

Here, the rate constant $k_1$ is known to have a value of $1.1 \times 10^{-2}$ $Pa^{-1}s^{-1}$, and a time duration during which the heavy water leaked in the air is changed into HDO at room temperature, at an atmospheric pressure, with a relative humidity of 50%, is about 50 ms, which is extremely fast. When heavy water flows into light water, a reaction takes place on the scale of nanoseconds. Thus, in the present invention, whether or not heavy water has leaked is detected and monitored by measuring the amount of HDO.

[Table 1] below shows transition lines and absorption cross sections of water molecules suitable for detecting a leakage of heavy water.

TABLE 1

| Discrimination | Isotopomer | Transition frequency ($cm^{-1}$) | Transition wavelength (nm) | Absorption cross section ($cm^2$, 0.02 atm) |
|---|---|---|---|---|
| A | $H_2^{16}O$ | 7176.197 | 1393.115 | $2.38 \times 10^{-22}$ |
|   | $HD^{16}O$ | 7176.419 | 1393.072 | $1.87 \times 10^{-19}$ |
| B | $H_2^{16}O$ | 7179.752 | 1392.425 | $1.13 \times 10^{-20}$ |
|   | $HD^{16}O$ | 7179.995 | 1392.378 | $1.25 \times 10^{-19}$ |
| C | $H_2^{16}O$ | 7183.879 | 1391.625 | $2.95 \times 10^{-23}$ |
|   | $HD^{16}O$ | 7183.973 | 1391.607 | $1.00 \times 10^{-19}$ |
|   | $H_2^{16}O$ | 7184.101 | 1391.582 | $7.79 \times 10^{-23}$ |
| D | $H_2^{16}O$ | 7190.738 | 1390.298 | $1.75 \times 10^{-20}$ |
|   | $HD^{16}O$ | 7191.039 | 1390.240 | $2.06 \times 10^{-19}$ |

Table 1 shows the frequencies and wavelengths of the transition lines used for detecting a leakage of heavy water and absorption cross sections of respective transition lines at an atmospheric pressure of 0.02, among transition lines according to the composition of the isotope of water molecules.

Oxygen isotopes composed of a water molecule along with hydrogen in nature have three types: $^{16}O$, $^{17}O$, and $^{18}O$. Among them, the component proportions of $^{17}O$ and $^{18}O$ are 0.037% and 0.204%, respectively, which are very small, but in order to precisely measure the rate of $H_2O$ and HDO, a $H_2^{17}O$ and $H_2^{18}O$ signal must not be present near the absorption spectrum of $H_2O$ and HDO, or if any, its size must be quite small.

In the near infrared ray having the frequency range shown in Table 1, the influence of the signal due to $^{17}O$ and $^{18}O$ is insubstantial, allowing for a precise component analysis.

In Table 1, 'A' and 'C' are suitable for detecting a leakage of heavy water into the secondary side such as the steam generator, and 'B' and 'D' are a transition line combination suitable for detecting a leakage of heavy water into the air.

FIG. 3 shows an absorption spectrum measured by injecting an air test sample from a location at which heavy water has leaked and an air test sample from a location at which heavy water has not leaked into the light absorption cell 12, in which a transition line of water molecular corresponds to 'B' in Table 1.

In FIG. 3, 101 denotes the spectrum of a test sample from the location without a leakage of heavy water in the air, and 102 denotes the spectrum of a test sample from the location with a leakage of heavy water. 103 denotes an absorption signal of $H_2O$ molecules appearing when a laser frequency is 7179.752 cm$^{-1}$, and 104 denotes an absorption signal of HDO molecules appearing when the laser frequency is 7079.995 cm$^{-1}$.

In nature, hydrogen isotopes include two types: H (or $^1$H) and D (or $^2$H). The component proportion of H is 99.985%, while that of D is merely 0.015%. Thus, when the absorption cross sections of the H$_2$O and HDO transition lines are similar like those of B in Table 1, the HDO signal (B) does not appear in the air test sample from the location without a leakage of heavy water, like the case of 101.

However, when heavy water has leaked, HDO is generated due to a hydrogen isotope exchange reaction, and an HDO signal (B') appears, as in the case 102, and an H$_2$O signal (A') is reduced when compared with the H$_2$O signal (A) in the case of 101.

Based on this principle, a leakage of heavy water can be detected with a high sensitivity by measuring the ratio between the HDO signal and the H$_2$O when heavy water has leaked in the air. Namely, if heavy water is not leaked, B/A is nearly 0, and if heavy water has leaked, B'/A' has a certain measurable value.

When a leakage occurs from a primary piping system of a nuclear reactor system, so heavy water has leaked in the air, a larger amount of the heavy water will have leaked into the air in the form of a heavy water aerosol having a particle diameter ranging from a few nm to a few μm, than will have leaked in the form of water vapor.

In this case, like heavy water vapor, the heavy water aerosol reacts with H$_2$O contained in the air, rapidly reducing H$_2$O in the air. Thus, in the present invention in which the HDO and H$_2$O signals are simultaneously measured to detect the ratio (B'/A') of the two signals, the leakage of heavy water in the form of heavy water aerosol can be also detected with a high sensitivity.

FIG. 4 is a graph illustrating an absorption spectrum measured by injecting HDO-contained natural light water into the light absorption cell 12, in which a transition line of water molecules corresponds to 'C' in Table 1.

In FIG. 4, 201 and 203 denotes absorption signals of the H$_2$O appearing when laser frequencies are 7184.101 cm$^{-1}$ and 7183.879 cm$^{-1}$, respectively, and 202 is an absorption signal of HDO molecules appearing when a laser frequency is 7183.973 cm$^{-1}$.

The detection of a small amount of HDO signal (i.e., 300 ppm) (a component portion of 'D' is 0.015%) included in natural light water shows that the sensitivity of the present invention is quite good.

The signals analyzed by the microprocessor 10 as described above are transmitted to the output unit 15 so as to be output in the form of numerical values or a graph (S600).

When one process of gathering and analyzing a test sample of a particular portion is completed, a process for analyzing a next test sample is prepared.

Namely, the analysis-completed test sample is removed from the light absorption cell 12, and the next sample is introduced and analyzed. In this case, if a leakage of heavy water is detected, the corresponding results are distinguishable.

As described above, the apparatus and method for detecting a leakage of heavy water according to the exemplary embodiments of the present invention can be extensively applied to various types of nuclear reactor systems. In other words, the apparatus and method for detecting a leakage of heavy water according to the exemplary embodiments of the present invention can be applicable to a commercial light water reactor using light water as primary cooling water as well as to a commercial heavy water type nuclear reactor system using heavy water as primary cooling water for directly cooling a nuclear reactor and a heavy water type research reactor system.

The applicability of the present invention to the heavy water reactor system is beyond question, and the reason for the feasibility of the application of the present invention to the light water reactor system is due to the fact that the amount of mixed heavy water included in light water (i.e., primary cooling water, used for the nuclear reactor system) increases gradually as the operational time of the nuclear reactor system increases (i.e., as operational hours are accumulated or pass by).

In other words, as the nuclear reactor system is operated, light water used as the primary cooling water is constantly exposed to radiation (i.e., radial rays) radiated from the nuclear reactor, and as a result, the density of mixed heavy water, contained in a relatively small amount of about 300 ppm in natural light water, increases to a level of approximately 3,000 ppm when 10 operational years have passed, ending in a situation wherein the heavy water density is higher by 10 fold than that of natural light water.

As described above, a leakage of heavy water can be detected by measuring the radio of the H$_2$O signal and the HDO signal obtained from the gathered test sample. Thus, even when light water including mixed heavy water with such a high density as mentioned above has leaked, it can be properly detected. As a result, the apparatus and method for detecting a leakage of heavy water according to the exemplary embodiments of the present invention allow for the precise detection of a leakage of primary cooling water in various nuclear reactor systems using light water, as well as heavy water, as their primary cooling water.

As set forth above, the apparatus for detecting a leakage of heavy water in a nuclear reactor system according to exemplary embodiments of the invention can detect in real time a leakage of heavy water into the air such as a leakage of heavy water from a pressure tube or a delayed neutron tube of a nuclear reactor system as well as a leakage of heavy water from a steam generator by using a highly sensitive laser absorption spectroscopy (LAS).

Also, the apparatus for detecting a leakage of heavy water in a nuclear reactor system can be manufactured at a low cost by employing a low-priced small diode laser and is readily portable thanks to its small size.

While the present invention has been shown and described in connection with the exemplary embodiments, it will be apparent to those skilled in the art that modifications and variations can be made without departing from the spirit and scope of the invention as defined by the appended claims.

What is claimed is:

1. An apparatus for detecting a leakage of heavy water in a nuclear reactor system by using a laser absorption spectroscopy (LAS), the apparatus comprising:
   a diode laser generating a laser beam and injecting the generated laser beam into a test sample placed in a light absorption cell;
   the light absorption cell accommodating the test sample therein;
   a vacuum pump adjusting a degree of vacuum of the light absorption cell;
   a test sample introduction unit gathering an air test sample from a location with a high possibility of a leakage of heavy water or a light water test sample from a secondary side and transferring it to the light absorption cell;
   an optical detector detecting a laser beam which has passed through the light absorption cell; and a microprocessor controlling the operation of the diode laser, the vacuum pump, the test sample introduction unit, and the optical detector, receiving a detect signal from the optical detector, and analyzing an absorption spectrum signal.

2. The apparatus of claim 1, further comprising:
an output unit connected with the microprocessor to output analysis results of the absorption spectrum analyzed by the microprocessor.

3. The apparatus of claim 1, wherein the light absorption cell is configured as a multi-pass cell comprising two or more optical mirrors, or is configured as an optical cavity.

4. The apparatus of claim 1, wherein the nuclear reactor system uses a heavy water reactor or a light water reactor.

5. An apparatus for detecting a leakage of heavy water in a nuclear reactor system by using a laser absorption spectroscopy (LAS), the apparatus comprising:
a diode laser generating a laser beam and injecting the generated laser beam into a test sample placed in a light absorption cell;
the light absorption cell accommodating the test sample therein;
a vacuum pump adjusting a degree of vacuum of the light absorption cell;
a test sample introduction unit gathering an air test sample from a location with a high possibility of a leakage of heavy water or a light water test sample from a secondary side and transferring it to the light absorption cell;
an optical detector detecting a laser beam which has passed through the light absorption cell; and
a microprocessor controlling the operation of the diode laser, the vacuum pump, the test sample introduction unit, and the optical detector, receiving a detect signal from the optical detector, and analyzing an absorption spectrum signal,
wherein the test sample introduction unit comprises a first test sample introduction part that gathers an air test sample from a location with a high possibility of a leakage of heavy water and transfers the gathered test sample to the light absorption cell and a second test sample introduction part that gathers a light water test sample of the secondary side of the nuclear reactor system and transfers the gathered light water test sample to the light absorption cell.

6. The apparatus of claim 5, wherein the first test sample introduction part comprises:
an intake tube introducing an air test sample from the location with a high possibility of a leakage of heavy water; and
an intake pump gathering a remote air test sample and injecting the gathered air test sample into the light absorption cell,
wherein a plurality of intake tubes are installed at several locations of the nuclear reactor system.

7. The apparatus of claim 5, wherein the second test sample introduction part is directly connected with a light water tube of a heat exchanger or a steam generator of the nuclear reactor system.

8. A method for detecting a leakage of heavy water in a nuclear reactor system by using a laser absorption spectroscopy (LAS), the method comprising:
gathering an air test sample from a location with a high possibility of a leakage of heavy water;
receiving and accommodating the gathered air test sample in a light absorption cell;
projecting a laser beam to the test sample-accommodated light absorption cell;
measuring the laser beam which has passed through the light absorption cell by using an optical detector; and
analyzing a signal measured by the optical detector.

9. The method of claim 8, further comprising:
after the measured signal is analyzed, outputting the analysis results through a monitor or a printing unit.

10. The method of claim 8, wherein the laser projected to the light absorption cell is a near infrared ray region having a frequency ranging from 5,000 $cm^{-1}$ to 10,000 $cm^{-1}$.

11. The method of claim 8, wherein the nuclear reactor system uses a heavy water reactor or a light water reactor.

12. A method for detecting a leakage of heavy water in a nuclear reactor system by using a laser absorption spectroscopy (LAS), the method comprising:
gathering an air test sample from a location with a high possibility of a leakage of heavy water;
receiving and accommodating the gathered air test sample in a light absorption cell;
projecting a laser beam to the test sample-accommodated light absorption cell;
measuring the laser beam which has passed through the light absorption cell by using an optical detector; and
analyzing a signal measured by the optical detector,
wherein, in analyzing the signal measured by the optical detector, whether or not heavy water has leaked is determined based on a relative change in a rate of the detect signal detected from a pre-set particular wavelength.

13. A method for detecting a leakage of heavy water in a nuclear reactor system by using a laser absorption spectroscopy (LAS), the method comprising:
gathering a light water test sample of a secondary side of a nuclear reactor system;
receiving and accommodating the gathered light water test sample in a light absorption cell;
projecting a laser beam to the test sample-accommodated light absorption cell;
measuring the laser beam which has passed through the light absorption cell by using an optical detector; and
analyzing a signal measured by the optical detector.

14. The method of claim 13, further comprising:
after the measured signal is analyzed, outputting the analysis results through a monitor or a printing unit.

15. The method of claim 13, wherein the laser projected to the light absorption cell is a near infrared ray region having a frequency ranging from 5,000 $cm^{-1}$ to 10,000 $cm^{-1}$.

16. The method of claim 13, wherein the nuclear reactor system uses a heavy water reactor or a light water reactor.

17. A method for detecting a leakage of heavy water in a nuclear reactor system by using a laser absorption spectroscopy (LAS), the method comprising:
gathering a light water test sample of a secondary side of a nuclear reactor system;
receiving and accommodating the gathered light water test sample in a light absorption cell;
projecting a laser beam to the test sample-accommodated light absorption cell;
measuring the laser beam which has passed through the light absorption cell by using an optical detector; and
analyzing a signal measured by the optical detector,
wherein, in analyzing the signal measured by the optical detector, whether or not heavy water has leaked is determined based on a relative change in a rate of the detect signal detected from a pre-set particular wavelength.

\* \* \* \* \*